United States Patent
Weissenböck et al.

(10) Patent No.: US 8,435,198 B2
(45) Date of Patent: May 7, 2013

(54) SUPPORT SHELL ASSEMBLY FOR SUPPORTING AND SPLINTING LEGS

(75) Inventors: Herbert Weissenböck, Feistritz am Wechsel (AT); Christine Frühwirt, Wiener Neustadt (AT); Christoph Kment, Vienna (AT)

(73) Assignee: IMA Integrated Microsystems Austria GmbH, Wiener Neustadt (AT)

( * ) Notice: Subject to any disclaimer, the term of this patent is extended or adjusted under 35 U.S.C. 154(b) by 82 days.

(21) Appl. No.: 13/202,149

(22) PCT Filed: Feb. 18, 2010

(86) PCT No.: PCT/AT2010/000046
§ 371 (c)(1),
(2), (4) Date: Aug. 18, 2011

(87) PCT Pub. No.: WO2010/094052
PCT Pub. Date: Aug. 26, 2010

(65) Prior Publication Data
US 2011/0301521 A1   Dec. 8, 2011

(30) Foreign Application Priority Data
Feb. 18, 2009  (AT) ................. A 275/2009

(51) Int. Cl.
*A61F 5/00*  (2006.01)

(52) U.S. Cl.
USPC ............................................. 602/23; 602/27

(58) Field of Classification Search .......... 602/5, 11–12, 602/16, 23–30; 128/882; 5/624, 626
See application file for complete search history.

(56) References Cited

U.S. PATENT DOCUMENTS

| 4,057,056 | A  | * | 11/1977 | Payton ........................... 602/11 |
| 4,539,982 | A  |   | 9/1985  | Bailly |
| 4,559,934 | A  | * | 12/1985 | Philipp ........................... 602/27 |
| 5,460,600 | A  |   | 10/1995 | Bieling |
| 5,761,834 | A  |   | 6/1998  | Grim et al. |
| 6,361,514 | B1 |   | 3/2002  | Brown et al. |
| 6,652,474 | B1 | * | 11/2003 | Quinn et al. ..................... 602/21 |
| 6,755,798 | B2 | * | 6/2004  | McCarthy et al. ............... 602/13 |
| 7,267,656 | B2 | * | 9/2007  | Cooper ........................... 602/27 |
| 2002/0128574 | A1 | | 9/2002  | Darby |
| 2006/0052734 | A1 | | 3/2006  | Evans et al. |
| 2006/0287622 | A1 | | 12/2006 | Goodwin |

FOREIGN PATENT DOCUMENTS

| DE | 10057286 A1 | 5/2002 |
| DE | 202006003245 U1 | 8/2007 |

(Continued)

OTHER PUBLICATIONS

International Search Report issued in International Application PCT/AT2010/000046.

*Primary Examiner* — Michael A. Brown
(74) *Attorney, Agent, or Firm* — Fitch, Even, Tabin & Flannery, LLP

(57) ABSTRACT

In a support shell assembly for supporting and splinting legs comprising a left and a right leg shell and a sole element that is fastened to the leg shells, wherein the leg shells and the sole element have fastening means for receiving a tensioning element, arranged within the support shell assembly (5) there is at least one layer of a 3D textile (1) comprising at least two layers of a textile material which are held at a defined and pressure-resilient distance from one another by flexible threads (FIG. 3).

18 Claims, 4 Drawing Sheets

FOREIGN PATENT DOCUMENTS

Figure 1:
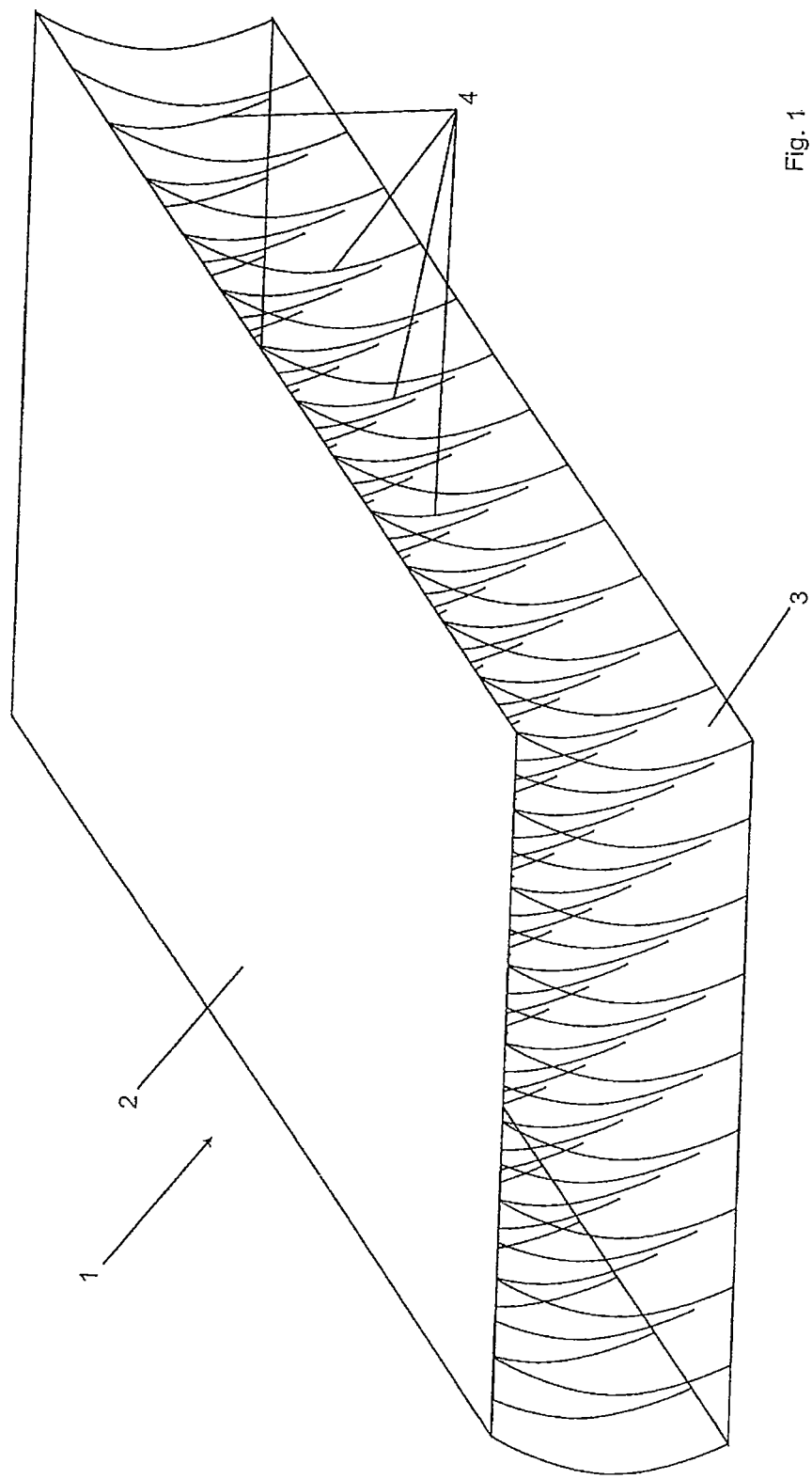

| | | | |
|---|---|---|---|
| EP | 0770368 | A1 | 5/1997 |
| FR | 2856917 | A1 | 1/2005 |
| WO | WO 97/23179 | A2 | 7/1997 |
| WO | WO 99/63915 | A1 | 12/1999 |
| WO | WO 2005/052235 | A1 | 6/2005 |

* cited by examiner

SUPPORT SHELL ASSEMBLY FOR SUPPORTING AND SPLINTING LEGS

CROSS-REFERENCE TO RELATED APPLICATIONS

This is a U.S. National Phase of International Application PCT/AT2010/000046, filed Feb. 18, 2010, and claims the benefit of foreign priority under 35 U.S.C. §119 from Austrian Patent Application A 275/2009, filed Feb. 18, 2009, the entire disclosures of which applications are hereby incorporated herein by reference.

The invention relates to a support shell assembly for supporting and splinting legs comprising a left and a right leg shell and a sole element that is fastened to the leg shells, wherein the leg shells and the sole element have fastening means for receiving a tensioning element.

In medicine today a plaster dressing is often dispensed with for supporting and splinting. In the simplest case a conventional plaster dressing consists of cotton and gypsum powder, whereby for the purposes of immobilisation and stabilisation the affected limbs or joints are wrapped with wet gypsum bandages which harden within a few minutes and after approximately twelve hours are fully load bearing. The drawbacks of a plaster dressing consist in the fact that the fitting of hardened plaster on a extremity can no longer be easily changed and as a result with too narrow a plaster there is a risk of negative effects on the blood supply and nerve function. Another disadvantage of plaster dressings is that they are not breathable, are not resistant to moisture and cannot be applied by a patient himself or herself. Also, plaster cannot be reused. Therefore, in the case of longer treatment, plastic fibres with artificial resin are now predominantly used. The advantages are more rapid hardening, lower weight and better resistance to moisture. However the costs are considerably higher and their environmental friendliness (in terms of production and disposal) is problematical. However plastic splits, also known as casts, have the same disadvantages as plaster dressing in terms of breathability and the negative effect on blood supply and nerve function through pressure points.

For decubitus prophylaxis so-called 3D textiles are increasingly being used in medicine. These innovative materials essentially comprise 2 textile surfaces held through special flexible fibres at a defined, pressure-resilient distance from each other. The extent of the pressure-resilience can be set by appropriate shaping of the textile, whereby the pressure-resilience can vary over the area of the textile. Such 3D textiles are successfully in use in decubitus mattresses, also antidecubitus mattresses, used in nursing to prevent or treat pressure sore in patients, primarily through reducing the maximum contact pressure. In addition to the functional advantage of progressive pressure distribution, 3D textiles also provide good ventilation and airflow through the large mesh width, and are low in weight due to their low density.

The aim of the invention is to create a support shell assembly for supporting and splinting legs which is easy to adapt to the extremity in question, is highly breathable, reusable, can be applied by the patient himself/herself, is light in weight and with which there is no risk of it negatively affecting the blood circulation and nerve function. The support shell assembly should also be able to be used as a medical walker, i.e. as a support or splint, with which the patient can walk, for which reason the stability of the support shell assembly is of utmost importance as it should not deform during walking so as not to reduce the splinting/supporting effect.

To achieve this objective a support shell assembly of the type set out in the introduction is designed in accordance with the invention in such a way that at least one layer of a 3D textile is arranged within the shell assembly. Through using at least one layer of 3D textile within the support shell assembly between the supported extremity and the hard support shell assembly the support shell assembly does not have to be fitted perfectly to the extremity in question as via the 3D textile the pressure distribution minimises all pressure peaks on the extremity. As there are no large pressure peaks acting on the extremity, the blood supply and nerve function of the extremity are restricted as little as possible. In spite of the fact that the extremity is in direct contact with the 3D textile, which advantageously can also be appropriately coated, ventilation of the extremity is guaranteed which particularly in the case of superficial wounds on the supported extremity speeds up the healing process. Special coatings of the 3D textile include wound-drying, antibacterial, disinfecting, wound healing-accelerating, non-adhesive and other coatings.

Preferably the support shell assembly in accordance with the invention is also designed so that the sole element is attached to the leg shells in a height adjustable manner. In this way the support shell assembly can be simply adapted for longer legs without part of the support shell assembly having to be replaced.

So that the support shell assembly can not only be adapted in terms of height but also in terms of the length and width of different feet, the support shell assembly is preferably designed so that the sole element is in several parts and can be adapted in length and width with extendable elements.

In order to achieve a therapeutic tiptoe position the support shell assembly is preferably further designed so that the heel area of the sole element is separately height-adjustable. In a particularly preferably manner this is achieved in that in the heel area the sole element has a recess for at least one wedge. Through applying the wedge in the heel area of the sole element the patient's heal can easily be raised by up to 80 mm compared to the front of the foot.

Advantageously the support assembly is developed further so that at least one essentially U-shaped carrier, running in the circumferential direction of the leg, is connected to or embedded in the 3D textile. As in a preferred manner the at least one essentially U-shaped carrier, running in the circumferential direction of the leg, is connected to or embedded in the 3D textile, the patient can in a simple manner firstly attach the 3D textile to his/her leg without the 3D textile losing its shape. As soon as the 3D textile is applied to the patient's foot he/she can easily step into the support shell assembly, which ensures that the 3D textile is correctly positioned on the leg. This carrier has a stabilising effect but can essentially be moulded and fitted to the shape of the leg.

Advantageously the support assembly is developed further so that preferably the at least one essentially U-shaped carried can be connected with the leg shells. As in a preferred manner the at least one essentially U-shaped carried can be connected with the leg shells, the support shell assembly gains stability in a simple manner. This of particular advantage if the at least one essentially U-shaped carrier is attached on the outside of the 3D textile, for example with a hook-and-loop fastener.

The total weight of the support shell assembly can be easily reduced in that the at least one essentially U-shaped carrier is made of strips of an anisotropically deformable synthetic film, e.g. LLDPE, or strips of an aluminium sheet.

To further increase the wearing comfort of the support shell assembly in accordance with the invention it is preferably designed so that the support shell assembly comprises a shin shell and a calf shell which are each connected to the leg shells and/or the sole element by means of the tension element. The shin shell is preferably shaped so that it prevents irritation of the shin and the calf shell is designed so that on the one hand it independently adjusts to different calf shapes and on the other hand supports the leg even when the heel is elevated.

Preferably the support shell assembly is further developed in such a way that the tensioning element is formed of tensioning bands or strings. The purpose of the tensioning element is to hold together the individual shells of the support shell assembly which are not directly connected to each other, to ensure stability and to secure the 3D textile against displacement at points at which it is not in contact with the support shell assembly between the supported extremity and the tensioning element.

Preferably the support shell assembly is further developed so the tensioning bands or tension strings can be tensioned with a roll-up device limiting the torque. As the tensioning bands or tensioning strings can preferably be tensioned with a roll-up device limiting the torque the support shell assembly can on the one hand be applied by the patient without distortion and on the other hand patient cannot apply the support shell assembly too tightly.

Preferably the support shell assembly is further designed so that the torque-limiting roll-up device can be attached by means of a detachable coupling to various points of the support shell assembly. When using a shin shell the roll-up device could for example be attached thereto. If a shin shell is not used the coupling points can be arranged in the left and right leg shell so the roll-up device can be attached on the left when using the support shell assembly on the left leg, and on the right side when used on the right leg.

Rapid removal of the support shell assembly can preferentially be achieved in that, in conformity with to a preferred form of embodiment of the support shell assembly, the tensioning element is fitted with a rapid release fastening. By opening the rapid release fastening the support shell assembly can be loosened whereby the supported extremity is released. If the 3D textile is firmly attached to the support shell assembly the patient can remove the leg from the support shell assembly without effort, whereas if the 3D textile is attached to the extremity it must removed separately after taking the extremity out of the support shell assembly.

Due to the fact that, in conformity with a preferred embodiment of the support shell assembly, the support shell assembly is made of a high-impact/impact resistant plastic, more particular a fibreglass-epoxy resin composite material, it is lightweight, stable and practically indestructible. In order to avoid wearing of the sole section in everyday use or to compensate for impacts on the sole section, the sole section is preferably rubberised or coated.

For additional breathability of the support shell assembly it is preferably further developed so that the 3D textile is covered with a breathable functional textile.

Preferably the support shell assembly in accordance with the invention is developed further in that for the 3D textile materials of different compressive strength are used, as a result of which it is possible to suitably select the compressive strength of the material for the 3D textile in various areas of the support shell assembly in accordance with the required circumstances.

Preferably forms of embodiment in which the compressive strength of the material for the 3D textile is approximately 160 N/cm depth, whereby in areas where the layers of material overlap the compressive strength at the same thickness is selected to be around half as much.

In order to ensure optimised support in the area of the front of the foot as well, in accordance with a preferred from of embodiment of the invention the support shell assembly is designed so that the support shell assembly comprises a front foot shell, possibly connected to the shin shell, and/or a heel shell. The shin shell and the front foot shell are generally designed in one piece and together from a front shell. All shell elements are connected to bother shells via band or straps on the U-shaped carrier.

In accordance with a preferred form of embodiment of the present invention the support shell assembly is further designed so that the tensioning bands or tensioning string can be tensioned with a calliper buckle.

The invention will be described in more detail below with the aid of the schematically shown example of embodiment in the drawing. FIG. 1 shows cross-section through a 3D textile, FIG. 2 shows a perspective view of a first embodiment of the support shell assembly, FIG. 3 shows a second embodiment of a support shell assembly with a shin and calf shell, and FIG. 4 show a further alternative embodiment of the support shell assembly in accordance with the invention.

If FIG. 1 a 3D textile is denoted with 1, wherein a first layer of a textile materials is denoted with 2 and a second layer of a textile material with 3. Between these layers spacers are denoted with 4 which are very thin and flexible and in an extension movement tend to return to their initial position. The spacers 4 are normally made of suitable synthetic materials such as polyesters. The two layers are thus connected to each other in a sprung manner and through adaptation of the shape, thickness and density of the spacers the 3D textile can be adapted to various circumstances. 3D textiles are also known as spacer fabrics. Spacer fabrics are double-surface textiles in which the warp-knitted surfaces are held at a distance from each other by spacing connection threads, known a pile threads. Spacer fabrics are machine-made goods/textiles expanded in the third dimension.

Figure 2:
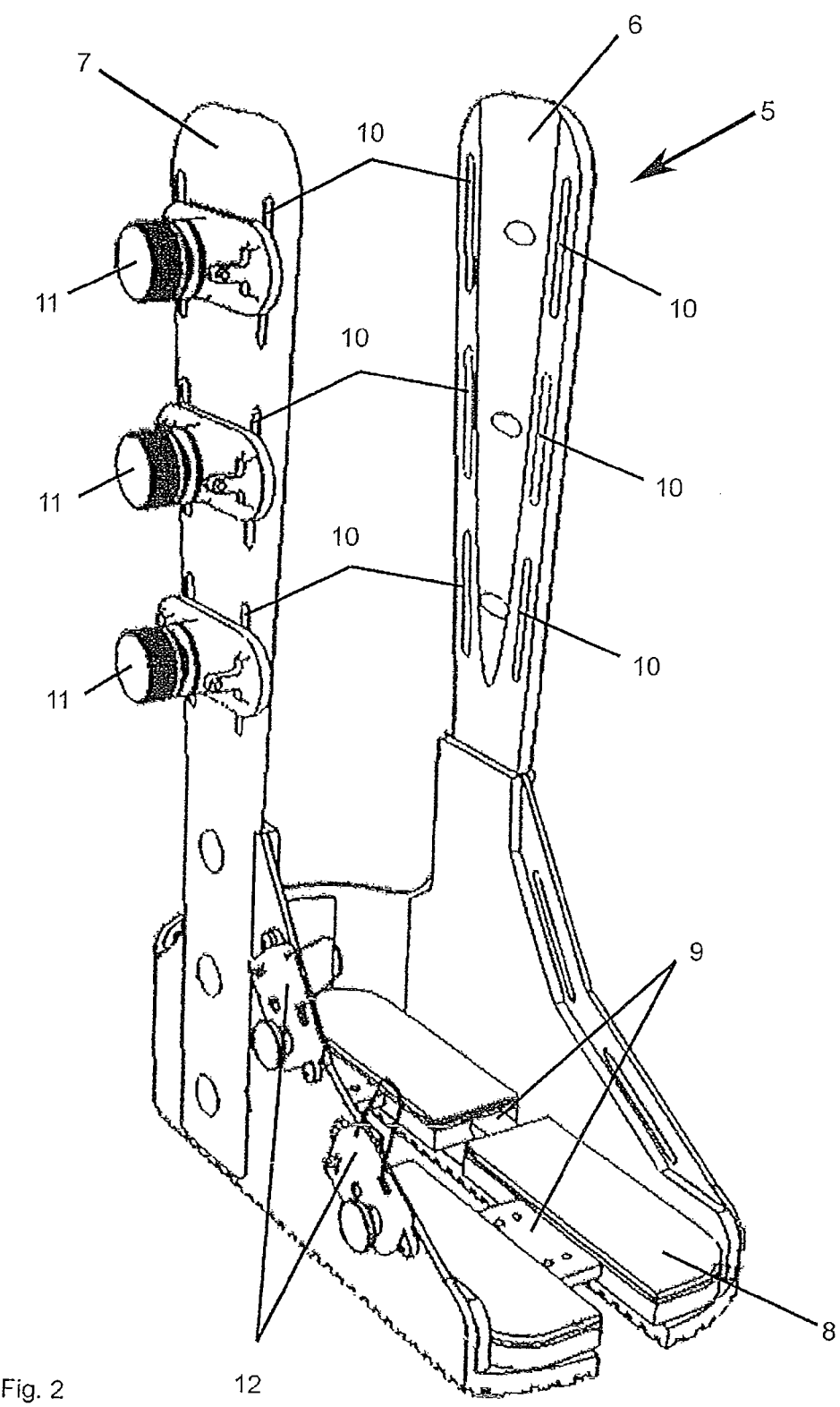

FIG. 2 shows a support shell assembly 5 which has a left and a right leg shell 6 and 7. A sole element 8 is connected to the leg shells 6 and 7 in a height-adjustable manner. The sole element 8 itself comprises four parts and can be adapted to the patient's foot in terms of length and width via extendable elements 9. The leg shells 6 and 7 and the sole element 8 have a number of elongated holes 10 through which in the simplest case the tensioning element can be directly passed. Preferable envisaged, however, are torque-limiting roll-up devices 11 and tensioning element guides 12 which can be attached in the elongated holes 10. With suitable guiding of the tensioning element one roll-up device 11 is sufficient, which tensions the tensioning element over the entire length of the support shell assembly. The tensioning element guides are designed so that the friction between the tensioning element guide 12 and the tensioning element is as low as possible so that the tensioning force is distributed evenly over the entire support shell assembly. Depending on whether the left or the right leg is splinted the roll-up device(s) 11 can be attached on the left or the right leg shell. The underside of the sole element 8 is profiled in order to improve grip when walking.

Figure 3:
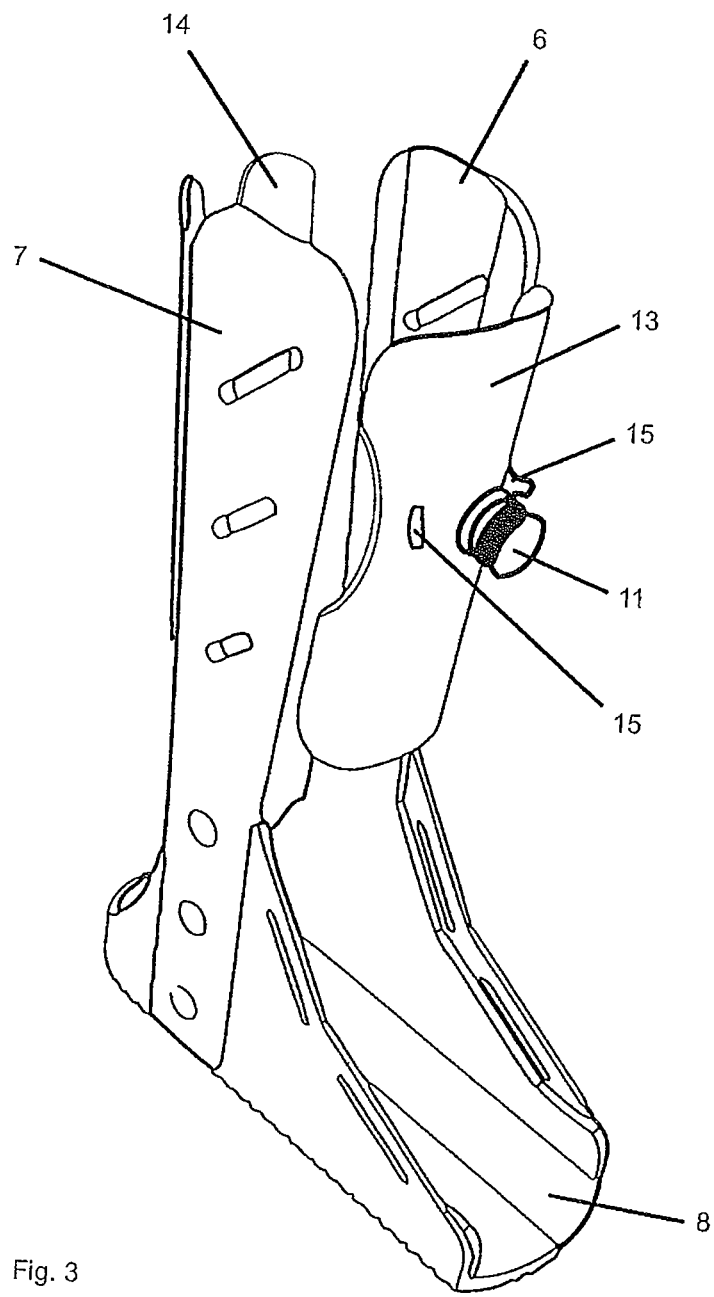
Figure 4:
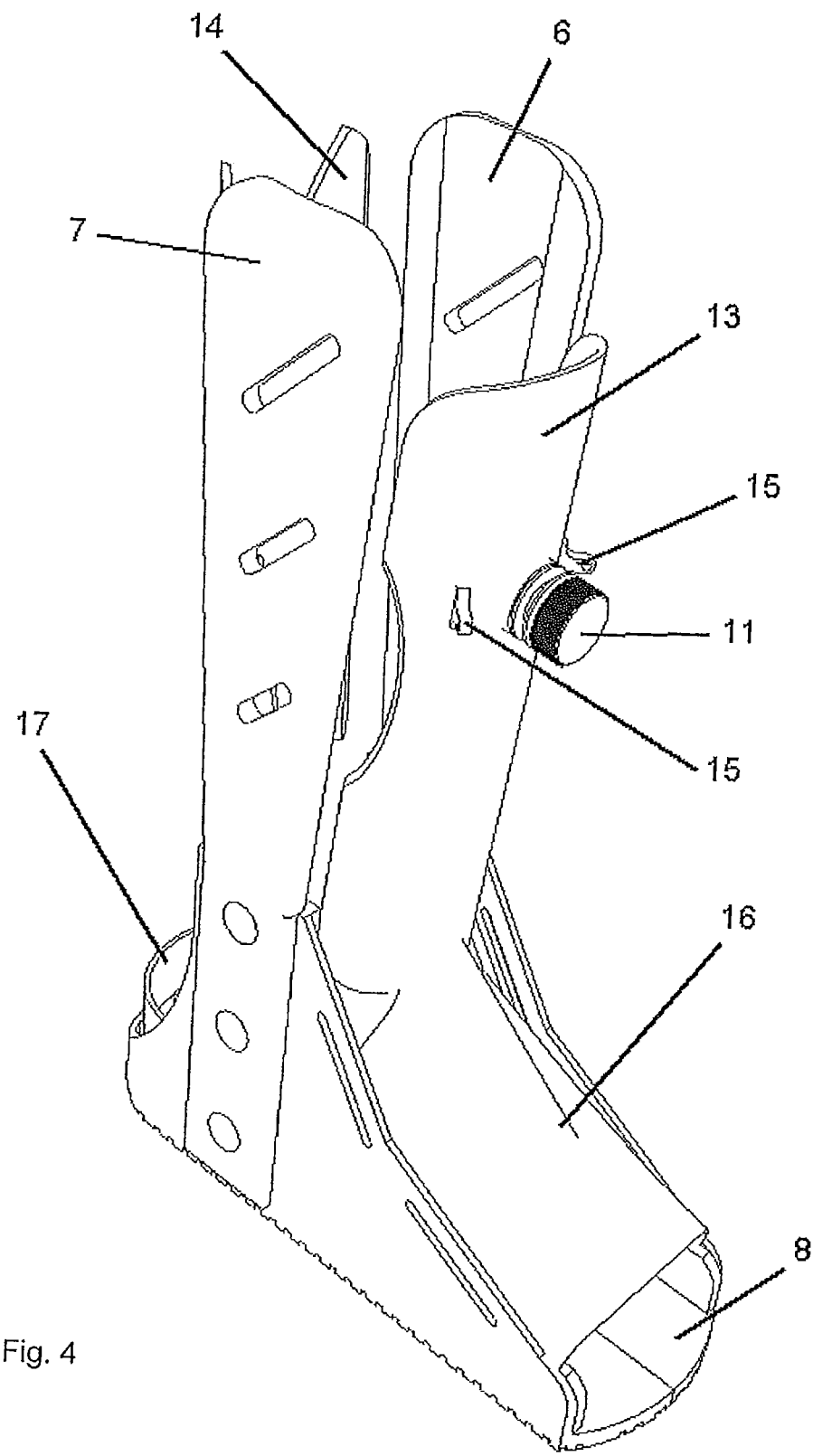

In FIG. 3 in addition to the left and the right leg shell 6, 7, a shin shell 13 and a calf shell 14 can also be seen. The roll-up device 11 in this embodiment is attached to the shin shell 13 on which two string guides 15 are also attached which ensure that the tensioning element is evenly rolled up from both sides.

FIG. 4 shows a further modified example of embodiment of the support shell assembly in accordance with the invention in which a front foot shell 16 is connected in one piece with the shin shell 13. In addition 17 denotes a heel shell. Such a design of the support shell assembly in accordance with the invention allows optimum support of the affected limbs and also provides increased protection against impact in the area of the front of the foot.

The invention claimed is:

1. Support shell assembly for supporting and splinting legs comprising a left and a right leg shell and a sole element that is fastened to the leg shells, wherein the leg shells and the sole element have fastening means for receiving a tensioning element, characterised in that arranged within the support shell assembly (5) is at least one layer of a 3D textile (1) comprising at least two layers of a textile material which are held at a defined and pressure-resilient distance from one another by flexible threads, that the support shell assembly (5) further comprises a shin shell (13) and/or a calf shell (14), which are each connected via the tensioning element to the leg shells (6, 7) and the sole element (8), and that the support shell assembly further comprises a front foot shell, which may be connected to the shin shell, and/or a heel shell.

2. Support shell assembly according to claim 1, wherein said sole element (8) is attached to the leg shells (6, 7) in a height-adjustable manner.

3. Support shell assembly according to claim 1, wherein said sole element (8) is designed in several parts and can be adapted in length and width with extendable elements (9).

4. Support shell assembly according to claim 1, wherein a hell area of said sole element (8) can be separately height adjusted.

5. Support shell assembly according to claim 1, wherein said sole element (8) has a recess in a heel area thereof for receiving at least one wedge.

6. Support shell assembly according to claim 1, wherein at least one essentially U-shaped carrier running in the circumferential direction of the leg is connected to or embedded in said 3D textile (1).

7. Support shell assembly according to claim 6, wherein said at least one essentially U-shaped carrier can be connected to the leg shells (6, 7).

8. Support shell assembly according to claim 6, wherein said at least one essentially U-shaped carried is made of strips of an anisotropicaly deformable synthetic film, e.g. LLDPE or strips of an aluminum sheet.

9. Support shell assembly according to claim 1, wherein said tensioning element is formed of tensioning bands or tensioning strings.

10. Support shell assembly according to claim 9, wherein said tensioning bands or tensioning strings are tensioned with a torque-limiting roll-up device (11).

11. Support shell assembly according to claim 10, wherein said torque-limiting roll-up device (11) can be attached via a detachable coupling to various parts of the support shell assembly.

12. Support shell assembly according to claim 1, wherein said tensioning element is fitted with a rapid-release fastening.

13. Support shell assembly according to claim 1, wherein said support shell assembly (5) is made of an high-impact or impact-resistant synthetic material.

14. Support shell assembly according to claim 1, wherein said 3D textile (1) is covered with a breathable functional textile.

15. Support shell assembly according to claim 1, wherein said 3D textile has areas of different compressive strength.

16. Support shell assembly according to claim 15, wherein the compressive strength of the material for the 3D textile is approximately 160N/cm depth, whereby in areas where the layers of material overlap the compressive strength at the same thickness is selected to be around half as much.

17. Support shell assembly according to claim 9, wherein said tensioning bands or tensioning string are tensioned with a caliper buckle.

18. Support shell assembly according to claim 1, wherein said support shell assembly (5) is made of a fiberglass-epoxy resin composite material.

\* \* \* \* \*